(12) United States Patent
Marivoet et al.

(10) Patent No.: US 10,324,044 B2
(45) Date of Patent: Jun. 18, 2019

(54) APPARATUS, METHOD AND COMPUTER PROGRAM PRODUCT FOR DEFECT DETECTION IN WORK PIECES

(71) Applicant: KLA-Tencor Corporation, Milpitas, CA (US)

(72) Inventors: Tom Marivoet, Erps-Kwerps (BE); Carl Truyens, Rotselaar (BE); Christophe Wouters, Balen (BE)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/200,613

(22) Filed: Jul. 1, 2016

(65) Prior Publication Data

US 2016/0313257 A1 Oct. 27, 2016

Related U.S. Application Data

(63) Continuation of application No. PCT/US2015/064100, filed on Dec. 4, 2015.
(Continued)

(51) Int. Cl.
*G01N 21/95* (2006.01)
*G01R 31/01* (2006.01)
(Continued)

(52) U.S. Cl.
CPC ..... *G01N 21/9501* (2013.01); *G01N 21/8806* (2013.01); *G01N 21/95* (2013.01);
(Continued)

(58) Field of Classification Search
CPC H01L 22/12; G01N 21/9505; G01N 21/9501; G01N 21/95
See application file for complete search history.

(56) References Cited

U.S. PATENT DOCUMENTS 4,689,491 A 8/1987 Lindow et al.
4,891,530 A 1/1990 Hatji
(Continued)

FOREIGN PATENT DOCUMENTS

CN 2791639 6/2006
CN 203011849 6/2013
(Continued)

OTHER PUBLICATIONS

EP Supplementary Search Report dated Mar. 5, 2018 for European Patent Application No. 15865251.1.
(Continued)

*Primary Examiner* — Marcus H Taningco
(74) *Attorney, Agent, or Firm* — Suiter Swantz pc llo

(57) ABSTRACT

An apparatus, a method and a computer program product for defect detection in work pieces is disclosed. At least one light source is provided and the light source generates an illumination light of a wavelength range at which the work piece is transparent. A camera images the light from at least one face of the work piece on a detector of the camera by means of a lens. A stage is used for moving the work piece and for imaging the at least one face of the semiconductor device completely with the camera. The computer program product is disposed on a non-transitory, computer readable medium for defect detection in work pieces. A computer is used to execute the various process steps and to control the various means of the apparatus.

22 Claims, 11 Drawing Sheets

Related U.S. Application Data

(60) Provisional application No. 62/088,284, filed on Dec. 5, 2014, provisional application No. 62/154,109, filed on Apr. 28, 2015.

(51) Int. Cl.
  *G01R 31/26* (2014.01)
  *G01R 31/28* (2006.01)
  *G01N 21/88* (2006.01)
  *G01N 21/956* (2006.01)

(52) U.S. Cl.
  CPC ... *G01N 21/9505* (2013.01); *G01N 21/95684* (2013.01); *G01R 31/01* (2013.01); *G01R 31/26* (2013.01); *G01R 31/28* (2013.01)

(56) References Cited

U.S. PATENT DOCUMENTS

| | | | |
|---|---|---|---|
| 6,339,337 | B1 | 1/2002 | Matsuda et al. |
| 6,384,415 | B1 | 5/2002 | Suzuki et al. |
| 6,529,018 | B1 | 3/2003 | Stevens |
| 8,154,718 | B2 | 4/2012 | Graf et al. |
| 8,224,062 | B2 | 7/2012 | Ohkura et al. |
| 8,532,364 | B2 | 9/2013 | Urban et al. |
| 9,786,045 | B2 * | 10/2017 | Hayashi ............... G06T 7/001 |
| 2002/0149765 | A1 | 10/2002 | Fujii et al. |
| 2004/0207836 | A1 * | 10/2004 | Chhibber ............ G01N 21/4738 356/237.4 |
| 2006/0278831 | A1 * | 12/2006 | Matsumoto ............ G01N 21/59 250/341.1 |
| 2007/0257192 | A1 * | 11/2007 | Nishino ............. G01N 21/9505 250/341.4 |
| 2009/0166517 | A1 | 7/2009 | Moribe et al. |
| 2009/0220864 | A1 | 9/2009 | Tanabe |
| 2010/0014083 | A1 * | 1/2010 | Ueno ................. G01N 21/9501 356/364 |
| 2011/0025838 | A1 | 2/2011 | Ninomiya |
| 2011/0122403 | A1 * | 5/2011 | Jang ....................... G01N 21/94 356/237.1 |
| 2012/0307236 | A1 | 12/2012 | Ortner et al. |
| 2013/0027543 | A1 * | 1/2013 | Boeykens .......... G01R 31/2635 348/92 |
| 2014/0063799 | A1 | 3/2014 | Voges et al. |
| 2014/0233014 | A1 | 8/2014 | Lei |
| 2015/0253256 | A1 * | 9/2015 | Zhou .................. G01N 21/9501 356/237.5 |

FOREIGN PATENT DOCUMENTS

| | | |
|---|---|---|
| CN | 103376259 | 10/2013 |
| EP | 1001460 | 5/2001 |
| EP | 2401603 A1 | 1/2012 |
| EP | 2699071 | 2/2014 |
| GB | 1214870 | 12/1970 |
| JP | 2003139523 | 5/2003 |
| JP | 2007171149 | 7/2007 |
| JP | 2012083125 | 4/2012 |
| JP | 2013015428 | 1/2013 |
| JP | 2013036888 | 2/2013 |
| KR | 101385219 | 4/2014 |
| TW | 200907335 | 2/2009 |
| TW | 201129792 | 9/2011 |
| WO | 1998/037404 | 8/1998 |
| WO | 2004/072629 | 8/2004 |
| WO | 2009/021207 | 2/2009 |
| WO | 2010/097055 | 9/2010 |
| WO | 2014052811 A1 | 4/2014 |

OTHER PUBLICATIONS

Examination Report dated Dec. 20, 2018 for EP Patent Application No. 15865251.1.

* cited by examiner

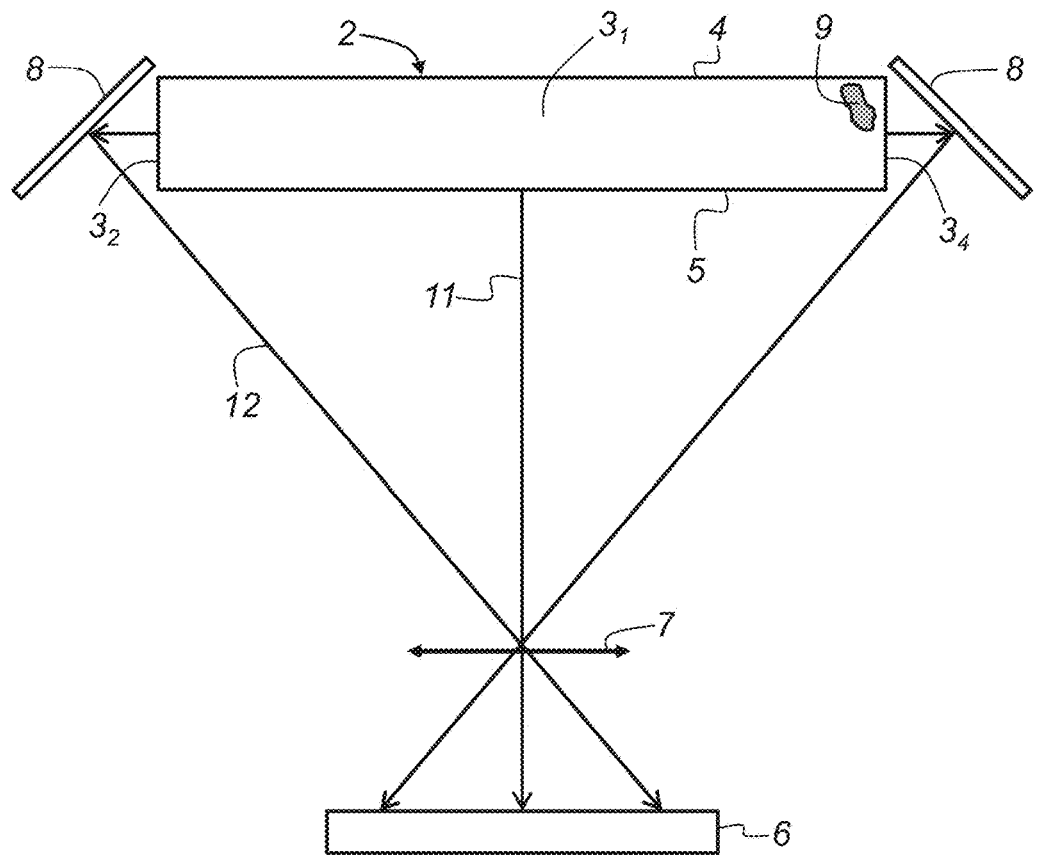
Prior Art  Fig. 1
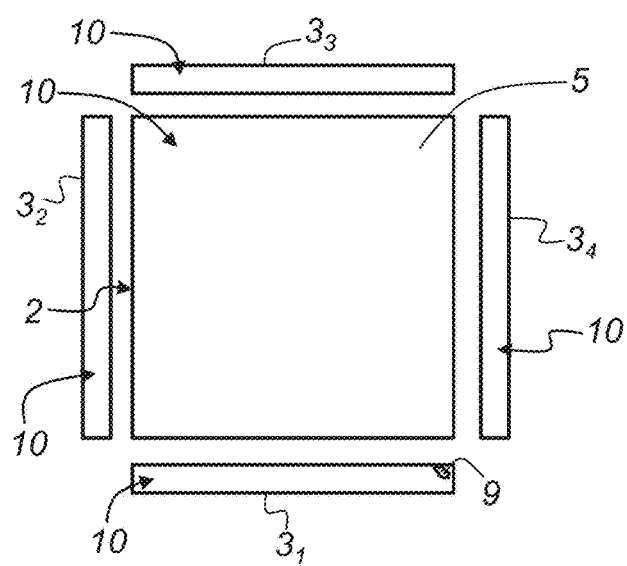
Fig. 2

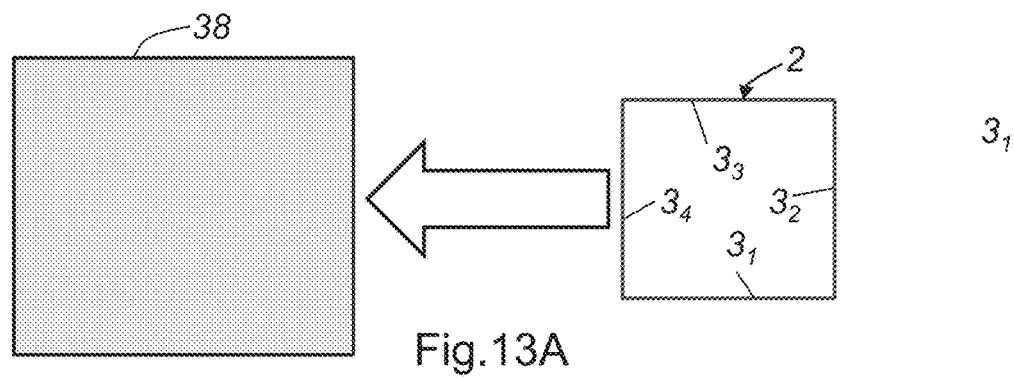
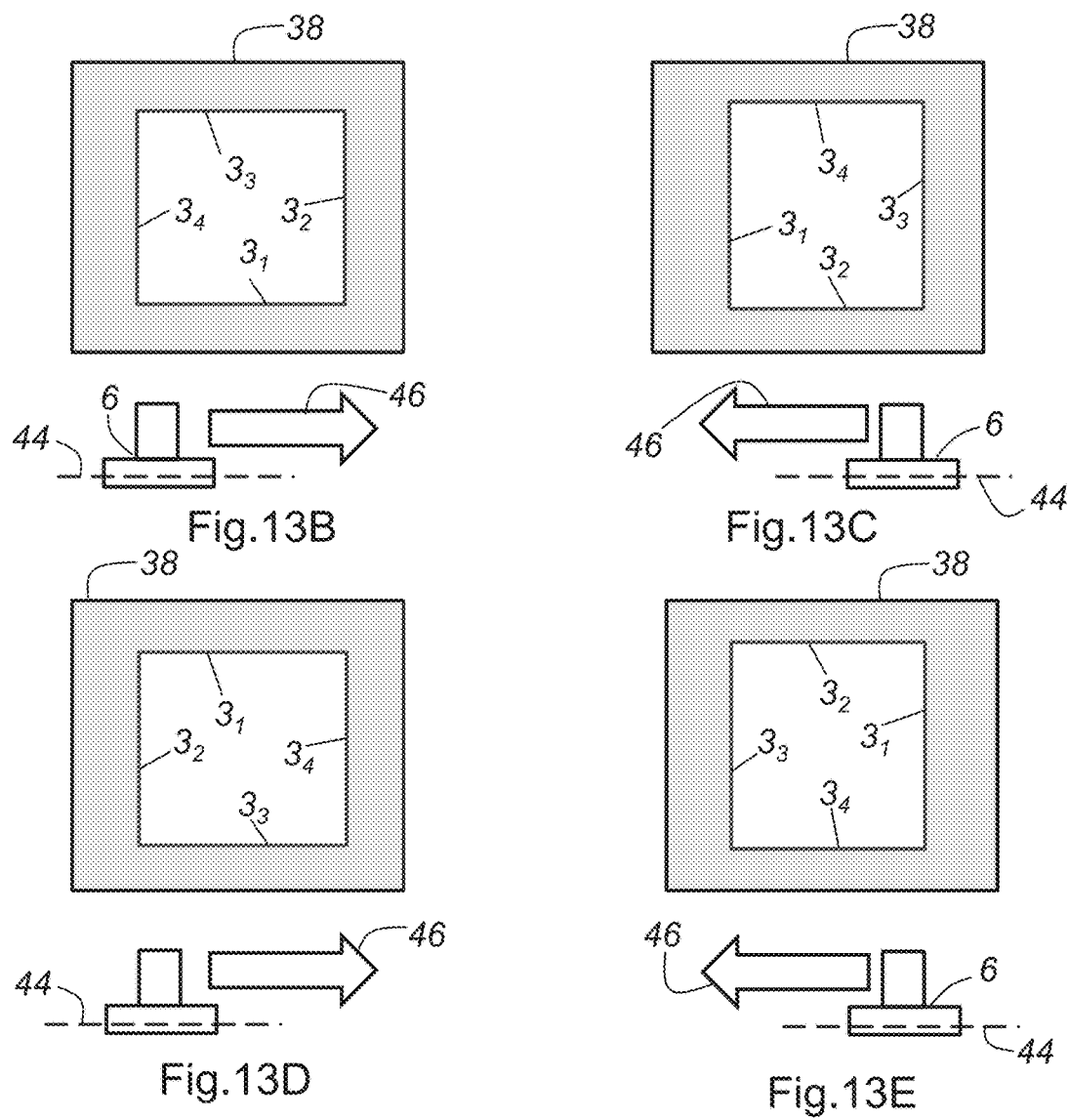

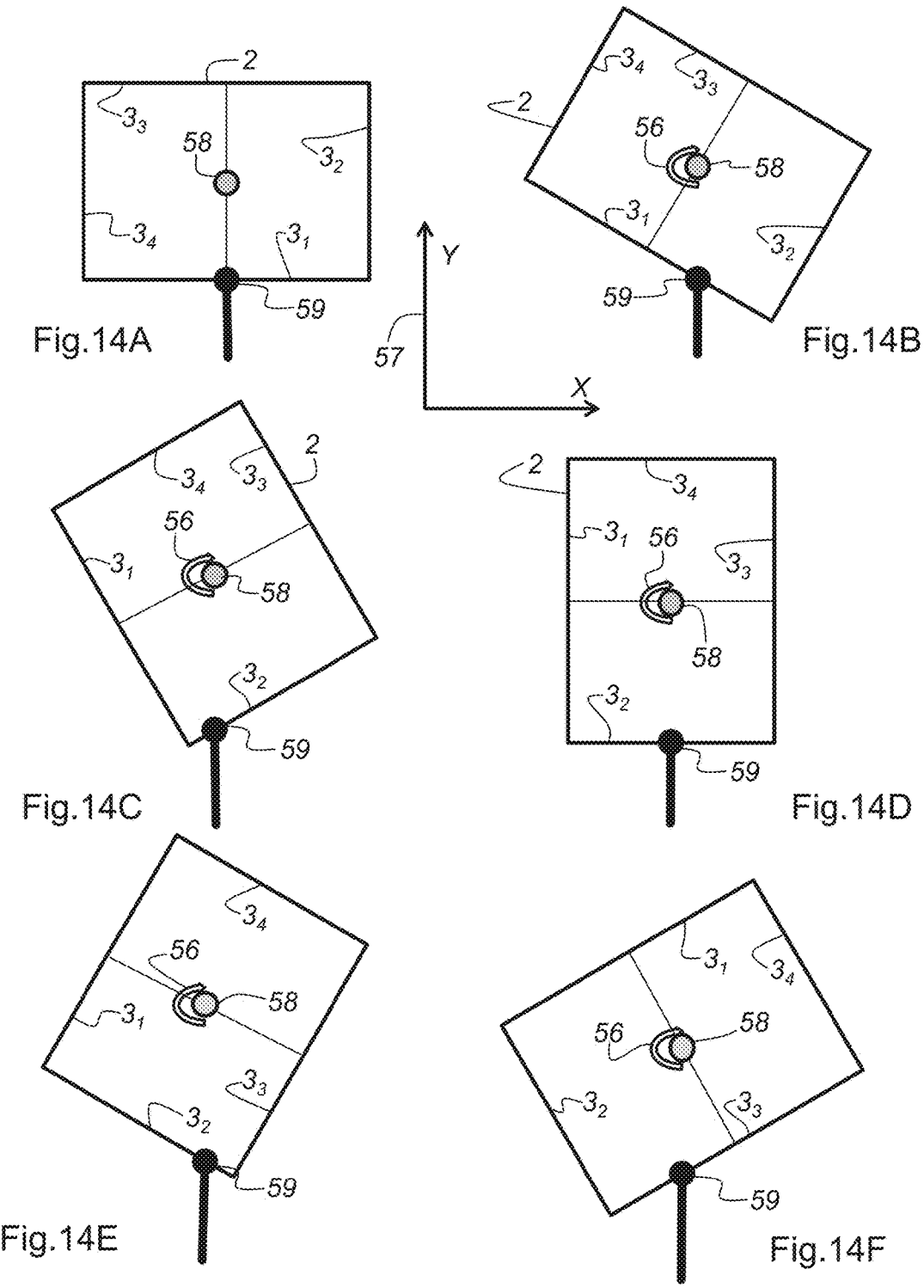

APPARATUS, METHOD AND COMPUTER PROGRAM PRODUCT FOR DEFECT DETECTION IN WORK PIECES

CROSS REFERENCE TO RELATED APPLICATIONS

This application is filed under 35 U.S.C. § 120 and § 365(c) as a continuation of International Patent Application Serial No. PCT/US2015/064100, filed on Dec. 4, 2015, which application claims the benefit under 35 U.S.C. § 119(e) of U.S. Provisional Patent Application No. 62/088,284 filed on Dec. 5, 2014 and U.S. Provisional Patent Application No. 62/154,109 filed on Apr. 28, 2015, which applications are incorporated herein by reference in their entireties.

FIELD OF THE INVENTION

The present invention refers to an apparatus for defect detection in work pieces.

Furthermore, the present invention refers to a method for defect detection in work pieces.

Additionally, the present invention refers to a computer program product disposed on a non-transitory computer readable medium, the product comprising computer executable process steps operable to control a computer for defect detection in work pieces.

BACKGROUND OF THE INVENTION

For example, U.S. Pat. No. 6,339,337 B1 discloses an infrared ray test for a semiconductor chip. The test is conducted by irradiating an infrared ray onto a bottom surface of a semiconductor chip, receiving the infrared ray reflected from a bonding pad, and displaying the image of the bonding pad on a monitor. The image obtained from the infrared ray has information whether the bonding pad itself or a portion of the silicon substrate underlying the bonding pad has a defect or whether or not there is a deviation of the bonding pad with respect to the bump.

Chinese utility model CN 2791639 (Y) discloses a detecting device, which is mainly used for detecting internal defects of semiconductor material of which the band gap is larger than 1.12 eV. The detecting device for detecting internal defects of semiconductor material is composed of an optical microscope, an infrared CCD camera, video cable, a simulation image monitor, a digital image collection card, a computer and analysis process and display software. Additionally, EP 2699071 A2 disclose an optoelectronic method for recording a heat diagram from the temperature distribution of land in which an infrared line scan system is used in an aircraft. The apparatus utilizes a rotary scanning mirror system receiving heat radiation through windows. The mirror system has four reflecting sides and is rotated about an axis by an electric motor. The radiation is directed by mirrors to an IR lens and then to a row of optoelectronic receiver elements. The row of receiver elements is parallel to the axis of rotation of the mirror system, each receiver element being individually connected by a lead and an amplifying device to a corresponding one of a number of luminescent diodes.

U.S. Pat. No. 8,154,718 B2 discloses a device to analyze micro-structured samples of a wafer. The aim of the device is to increase the possible uses of said devices, i.e. particularly in order to represent structural details, e.g. of wafers that are structured on both sides, which are not visible in VIS or UV because coatings or intermediate materials are not transparent. IR light is used as reflected light while creating transillumination which significantly improves contrast in the IR image, among other things, thus allowing the sample to be simultaneously represented in reflected or transmitted IR light and in reflected visible light.

Typical defects are side cracks created by the dicing process or embedded cracks created by internal stress in the device between the dielectric layer and the silicon structure.

FIG. 1 shows a prior art method for finding side defects 9 in a semiconductor device 2 by doing a four sided or a five sided inspection. The semiconductor device 2 has a first side face 31, a second side face 32, a third side face 33, a fourth side face 34, a top face 4 and a bottom face 5. In the setup of FIG. 1 a camera 6 with a lens 7 looks to the bottom face 5 of the semiconductor device 2. A mirror 8 is arranged under 45 degrees with each of the first side face 31, the second side face 32, the third side face 33 and the fourth side face 34 of the semiconductor device 2, respectively. In FIG. 1 only the mirrors 8 arranged with respect to the second side face 32 and the fourth side face 34 of the semiconductor device 2 are shown.

The setup of FIG. 1 is used to obtain an image 10 (see FIG. 2) of the first side face 31, the second side face 32, the third side face 33, the fourth side face 34 and the bottom face 5, respectively. Additionally, the setup of FIG. 1 has significant drawbacks. The optical length 11 of the bottom face 5 view differs from the optical length 12 of the first side face 31 view, the second side face 32 view, the third side face 33 view and the fourth side face 34 view. Therefore, the focus is always a trade-off between focus on the bottom face 5 of the semiconductor device 2 and focus on the first side face 31, the second side face 32, the third side face 33 and the fourth side face 34, respectively. Additionally, the image resolution of the four-sided view requires a large field of view and this will limit the pixel resolution that can be used. For side views <10µm there is no working setup available, even by using a high resolution camera of 20 or 25 megapixels. Therefore it is not possible to have good focus and a high resolution in order to discriminate a real defect from non-critical contamination.

FIG. 3 is another embodiment of a prior art set-up for detecting interior defects 9 (side defects) by looking onto the top face 4 of a semiconductor device 2. For detecting interior defects 9 (that are invisible from the outside) there is no solution for high volume inspection. There is a slow method by using IR light 13 and optics 14 and looking to the back face of the semiconductor device 2 ("IR back view"). A camera 6 detects the IR-light 15 returning from the semiconductor device 2. A schematic representation of an image 16, obtained with the setup of FIG. 3 is shown in FIG. 4. The "IR back view" method with IR light 13 for detecting the interior defects 9 has drawbacks as well. First of all the method is slow. It only exists as manual, low volume method. If one wanted to automate this and make it faster there is an important limitation in the size and the number of pixels of the available IR cameras 6. Additionally, it only works for a limited set of devices where there is a bare silicon side to apply the IR light. An increasing number of devices have a coating to protect the device, which coating is not transparent for IR light. A further drawback is the signal to noise ratio. The top face 4 of the semiconductor device 2 will also create a reflection which makes it hard to distinguish a top defect from an interior defect 9.

This prior art method, described above, has significant drawbacks by inspecting five sides of a work piece (singulated semiconductor device). One drawback is the differing focus between the side face and the bottom face of the work piece. The optical length is different for bottom and side view, therefore the focus is always a trade-off between focus on the bottom of the work piece and focus on the edges (side faces) of the work piece. A further drawback is the image resolution. A view of the four side faces requires a large field of view and this will limit the pixel resolution that can be used.

BRIEF SUMMARY OF THE INVENTION

It is an object of the invention to provide an apparatus which makes it possible to detect side defects and internal defects in singulated work pieces with a high resolution and to distinguish between actual defects and contaminations on the faces of the work pieces. Additionally, the apparatus should have high throughput in order to do time-efficient quality control on such workpieces.

The above object is achieved by an apparatus for defect detection in work pieces wherein the apparatus comprises at least one light source for providing an illumination light of a wavelength range at which the work piece is transparent; a camera with a lens, for imaging the light from at least one face on the work piece on a detector of the camera; and a stage for moving the work piece and for imaging the at least one face of the work piece completely.

The advantage of the inventive apparatus is that it possible to reliably detect side defects and internal defects in singulated work pieces, for example semiconductor devices, also known as die. The inventive apparatus can be used to do quality control on such work pieces with high throughput.

It is a further object of the invention to provide a method for detecting side defects and internal defects in singulated work pieces at a high resolution, so that one can distinguish between actual defects and contaminations on the faces of the work pieces. Additionally, the method should enable a high throughput in order to do quality control on such work pieces within a reasonable time.

This object is achieved by a method for defect detection in work pieces, the method comprising illuminating a portion of at least one face of the work piece with illumination light of a wavelength range at which the work piece is transparent; imaging light from the portion of the at least one face of the work piece on a detector of a camera; and carrying out a relative movement of a stage, which holds the work piece, and the camera, such that the at least one face of the work piece is imaged completely by the camera.

The advantage of the inventive method is that it is possible to reliably detect side defects and internal defects in singulated work pieces, for example semiconductor devices, also known as die. The inventive method can be used to do quality control on such work pieces with high throughput.

An object of the invention is as well to provide a computer program product disposed on a non-transitory computer readable medium to automatically detect side defects and internal defects in singulated work pieces (semiconductor devices) at a high resolution, so that one can distinguish between actual defects and contaminations on the faces of the work pieces. Additionally, the computer program should enable a high throughput in order to do quality control on such work pieces within a reasonable time.

The above object is achieved by a computer program product disposed on a non-transitory computer readable medium for defect detection in work pieces, the product comprising computer executable process steps operable to control a computer to place the work piece on a stage; illuminate at least one face of the work piece with illumination light of a wavelength range at which the work piece is transparent; direct light, from the at least one face of the work piece, with an optical setup to at least one line sensor of a camera for imaging a line of light of the at least one face of the work piece; move the stage, which holds the work piece, such that the at least one face of the work piece is imaged completely by the line sensor of the camera and is in the focus of the camera during the movement of the stage.

Typical defects to be detected by the present invention are side cracks created by the dicing process of the work pieces or embedded cracks created by internal stress in the work piece. In case the work piece is a semiconductor device, the internal stress can exist for example between the dielectric layer and the silicon structure. It is noted that the invention (apparatus, method and computer program) is not restricted to semiconductor devices and is applicable for side and internal defects in general.

Typically one would use infrared (IR) light to be able to penetrate through the silicon based semiconductor device, but the source of the light could change depending on the wavelength range for which the material of the work piece is transparent.

According to an aspect of the present invention, the at least one light source is arranged such that the illumination light is directed to one side face of the work piece and the camera receives the light exiting from a further side face of the work piece. This further side face of the work piece is opposite to the side face of the work piece which receives the illumination light, in order to obtain back-light illumination.

Another possibility is that the further side face of the work piece is oriented such to the side face of the work piece which receives the illumination light that a dark field image of the further side face is obtained.

A further aspect of the invention is that the at least one light source is arranged such that the illumination light is directed to a top face of the work piece, and the camera receives the light shining out of the top face of the work piece.

An advantageous embodiment of the invention is, if the detector of the camera is a line sensor and the camera is configured as a line scan camera. In the new apparatus or method the use of a line scan camera, which is perpendicular to the side face of the work piece (semiconductor device) creates images by moving the work pieces on a X,Y,Theta-stage. Through the inventive optical setup it is possible to create a simultaneous view of at least a portion of the top face and at least one side face of the work piece. This optical setup allows for coaxial and external illumination as well, so the two modes can have the same or individual illumination.

A lens of the camera images a line of light exiting from a side face of the work piece onto the line sensor. The exiting light originates from at least one light source arranged such that a back-light illumination is obtained.

A stage, which holds the work piece, is moved along a scan direction, which is perpendicular to the line to be imaged. With the scanning motion a complete image of at least one of the side faces of the work piece is generated.

It is also possible that a lens of the camera images a line of light from at least a portion of a top face of the work piece onto the line sensor, wherein the line of light is positioned adjacent to one of the side faces of the work piece, and the at least one light source is arranged such that the light from the top face is coaxial to the light directed onto at least a portion of the top face of the work piece. In order to generate an image of at least a portion of the work piece, a stage, which holds the work piece, is moved along a scan direction, which is perpendicular to the line to be imaged. Accordingly, a complete image of the at least one portion of the top face is obtained. The portion of the top face is adjacent to at least one of the side faces of the work piece.

The stage and the camera also can carry out a relative motion to capture, for example, the complete image of the respective face of the work piece. The scan of the respective face can be carried out with various speed profiles along the scan direction. A preferred embodiment is a constant velocity along the length of the respective face. The selection of a constant requires less software effort and provides best image quality. It is clear for a skilled person that the selection of a constant velocity does not block other speed profiles. Another embodiment is an accelerated and decelerated speed during the scan. Here a higher capture rate is obtained at the edges and a lower capture rate in the center of the respective side face.

According to an embodiment of the invention an optical setup is provided, which generates simultaneously an image of a line of light exiting from a side face of the work piece and an image of a line of light from a top face of the work piece. The image of the line of light from a top face is positioned adjacent to the line of light from the respective side face of the work piece. A front end of the optical setup carries a top mirror and a first and second bottom mirror. The top mirror captures an image of the line of light from a portion of the top face of the work piece. The first bottom mirror and the second bottom mirror capture an image of a line of light exiting from a side face of the work piece. The inventive optical setup is designed such that the image of a line of light exiting from a side face of the work piece and the image of a line of light from a top face of the work piece are in focus simultaneously.

According to an embodiment of the invention, the light from at least one light source can be coupled separately to one side face of the work piece and the top face of the work piece.

It is advantageous that a light guide is positioned between the at least one light source and a top face and/or a respective side face of the work piece.

The work piece can be a singulated semiconductor device. In this case, the wavelength range of the illumination light is the wavelength range of IR light, because silicon based semiconductor devices are transparent for IR light.

The inventive apparatus has unique advantages. Two views can be combined. There is no need to take two images with a separate camera. By combining the two views information can be correlated during the image processing between the views leading to a higher capture rate for defects and a lower nuisance rate for noise. High resolution images are obtained by using the line scan camera. It is possible to create images with a higher resolution compared to normal matrix cameras. When using IR light one can find interior defects and/or improve the signal to noise ratio for specific defects. The top view (image of a portion of the top face) may be done under an angle as well in order to create a darkfield-like inspection mode.

The inventive method shows advantageous effects, for example in case the work pieces are semiconductor devices. With the inventive method it is possible to create images of the defects by using IR light that travels through the semiconductor device under inspection and by looking directly at one side face of the semiconductor device. For both the light source and the camera a perpendicular setup (looking/shining straight to the edges) or an angular setup can be used. Because of the high refractive index of silicon ($n=3.5$ for $\lambda=1200$ nm) and the rough edge of the device almost all light will go into the device. While the rays will travel under small angles through the device they will exit the device at the other side face as a diffuse ray of lights. In this way the device itself acts like a diffuse illumination.

The inventive method uses in one embodiment the physical characteristic of silicon (which is the base material for all semiconductor devices) that silicon becomes transparent for light with wavelengths above 1200 nm.

Based on this, the method builds further onto the "IR back view" but because the device itself acts like a diffuse illuminator the inventive method increases signal to noise and creates possibilities for fast inspection solutions. Typically, edge variations of the dicing process are smoothed out by the diffuse rays of lights. Material defects (like e.g. the crack which should be detected) will result in high contrast since that internal part of the semiconductor device will not receive light and will hence show as a dark part on the diffuse illuminating device.

One important technical aspect of the present invention is that the edges of the semiconductor devices are not nice and clean (due to the dicing process of the semiconductor devices); therefore the light will not travel straight and predictably through the semiconductor devices but rather gets scrambled creating a diffuse illuminator. Another important technical aspect is that by looking only at the side face, the area to inspect becomes factors smaller than by looking at the whole device (be it with the "IR back view" or the "5 sided solution") and this creates opportunities to increase the resolution (capture smaller defects) and do faster inspection (because images can still be a lot smaller than for the other methods).

According to an embodiment the illumination light is applied on one side face of the semiconductor device; since the edges are bare silicon (from the dicing process) the light propagates through the semiconductor device. Since the edge of the device is rough (due to the dicing process), light rays will not travel straight through the device. When, reaching the other side face of the semiconductor device, the rays incident under a small angle (approx. <17 deg) will get transmitted outside the semiconductor device. Rays with angles +/−90 degree make the edge of semiconductor device shine like a diffuse illuminator. However, when reaching an interior defect or a side crack the normal light propagation is blocked resulting in 'defective' part in the diffuse illuminating device and hence a high contrast dark blob in the camera image. The crack is typically a disturbance in the silicon structure. At this disturbance the light is reflected and does not propagate. Because of this the camera will see no light coming through at this location.

Another embodiment for carrying out the inspection of the semiconductor device uses the same principles. Here the IR-light shines through the semiconductor device in order to provide an "angular side view". IR light is sent into the sample under an angle. Interior cracks block light and change the normally diffuse illumination from the rough edge. The angular side view offers a large resolution but still makes fast inspection possible. Each internal or side defect appears bigger and with higher contrast as such defects block normal internal light propagation. The diffuse IR light shining out of the semiconductor device has a reduced response to external contamination and hence increases the signal to noise ratio for the real defects.

When moving the focus inside the semiconductor device one can resolve interior defects further away from the edge. This way one can even scan through the complete semiconductor device.

According to the inventive method, the illumination light of the at least one light source is directed to one side face of the work piece. Light exiting from a further side face of the work piece is imaged with the camera. It is preferred that the camera images the light exiting from the further side face of the work piece onto a line sensor by means of a lens.

Another embodiment of the invention is that the illumination light of the at least one light source is directed to a top face of the work piece. The camera images the light shining out of the top face of the work piece by means of a lens. It is preferred that the camera images the light exiting from the top face of the work piece onto a line sensor by means of a lens.

A further embodiment of the invention is that with an optical setup a line image of light exiting from a side face of the work piece and a line image of light from a portion of a top face of the work piece are simultaneously generated. The portion of the top face to be detected is positioned adjacent to the respective side face of the work piece.

According to one embodiment of the inventive method, there is one possibility for moving a stage for imaging at least two side faces and the respective portion of the top face of the work piece. The inventive method comprises a) carrying out a linear, relative movement between the stage with the work piece and the camera, so that an image plane of the camera is parallel to one of the side faces; b) rotating the stage with the work piece; and c) repeating steps a) and b) until all side faces of the work piece are imaged by the camera.

The linear, relative movement between the stage and the camera can be realized by a linear movement of the camera only. The linear movement of the camera is oriented in opposite directions between the rotating steps.

According to a further embodiment of the inventive method, there is one possibility for moving a stage for imaging at least two side faces and the respective portion of the top face of the work piece. The inventive method comprises: rotating the stage and in parallel carrying out a movement of the stage in the X/Y-plane, such that a focus point of the camera is kept on the respective side face during the rotational movement of the stage.

According to a further aspect of the invention, a computer program product is provided which is disposed on a non-transitory computer readable medium for defect detection in work pieces, the product comprising computer executable process steps operable to control a computer to place the work piece on a stage; illuminate at least one face of the work piece with illumination light of a wavelength range at which the work piece is transparent; direct light from the at least one face of the work piece to at least one line sensor of a camera by means of an optical setup, for imaging a line of light of the at least one face of the work piece; and move a stage, which holds the work piece, such that the at least one face of the work piece is imaged completely by the line sensor of the camera and is in focus of the camera during the movement of the stage.

As already mentioned above, according to one embodiment of the inventive method a line scan camera is used, which is perpendicular to the side face of the semiconductor device. Images are created by moving the semiconductor devices on a X,Y,Theta-stage. Through a custom optics a simultaneous view is created of at least a portion of the top face and a side face of the semiconductor device. This optical setup also allows for coaxial and external illumination, so the two modes can have the same or individual illumination. The line scan camera setup guarantees high resolution images which would be impossible by an area scan camera. By combining the two views of the at least one side face and the top face, the images contain much more information to extract the exact location and origin of the defects in the semiconductor device. By the integration on a moving stage setup, a high speed inspection can still be obtained although one receives two high resolution views.

The embodiment with the camera with the line sensor has unique advantages. Two views are combined and consequently there is no need to take two images with a separate camera. And by combining the two views information can be correlated during the image processing between the views leading to a higher capture rate for defects and a lower nuisance rate for noise. By using the line scan camera it is possible to create images with a higher resolution compared to normal matrix cameras.

The semiconductor devices, which are subjected to inspection, are typically used in mobile devices. The side cracks mentioned in the description above lead to customer returns entailing high costs for the device manufacturers, who thus are under a lot of pressure from their customers to do automated inspection and detect these side defects. Moreover, devices with such defects might still pass electrical tests, but often become early failures in the field (e.g. when the mobile phone is dropped). As explained, it is clear that the current methodologies are inadequate since they still miss defects in the semiconductor device (which are a risk for customer returns) while they reject good devices by triggering on non-important defects (which leads to a loss of money for the manufacturer).

BRIEF DESCRIPTION OF THE DRAWINGS

Below, the invention and its advantages will be further described with reference to the accompanying figures in which:

FIG. 1 is a prior art set-up for detecting interior defects by looking at the sides of a semiconductor device;

FIG. 2 is a schematic representation of an image obtained by the set-up shown in FIG. 1;

FIG. 13A is a schematic representation of an embodiment of a linear and rotational scanning mode of the semiconductor device;

FIG. 13B is a schematic representation of an embodiment of a linear and rotational scanning mode of the semiconductor device;

FIG. 13C is a schematic representation of an embodiment of a linear and rotational scanning mode of the semiconductor device;

FIG. 13D is a schematic representation of an embodiment of a linear and rotational scanning mode of the semiconductor device;

FIG. 13E is a schematic representation of an embodiment of a linear and rotational scanning mode of the semiconductor device;

FIG. 14A is a schematic representation of an embodiment of a combined linear and rotational scanning motion of the semiconductor device;

FIG. 14B is a schematic representation of an embodiment of a combined linear and rotational scanning motion of the semiconductor device;

FIG. 14C is a schematic representation of an embodiment of a combined linear and rotational scanning motion of the semiconductor device;

FIG. 14D is a schematic representation of an embodiment of a combined linear and rotational scanning motion of the semiconductor device;

FIG. 14E is a schematic representation of an embodiment of a combined linear and rotational scanning motion of the semiconductor device; and FIG. 14F is a schematic representation of an embodiment of a combined linear and rotational scanning motion of the semiconductor device.

DETAILED DESCRIPTION OF THE INVENTION

Figure 3:
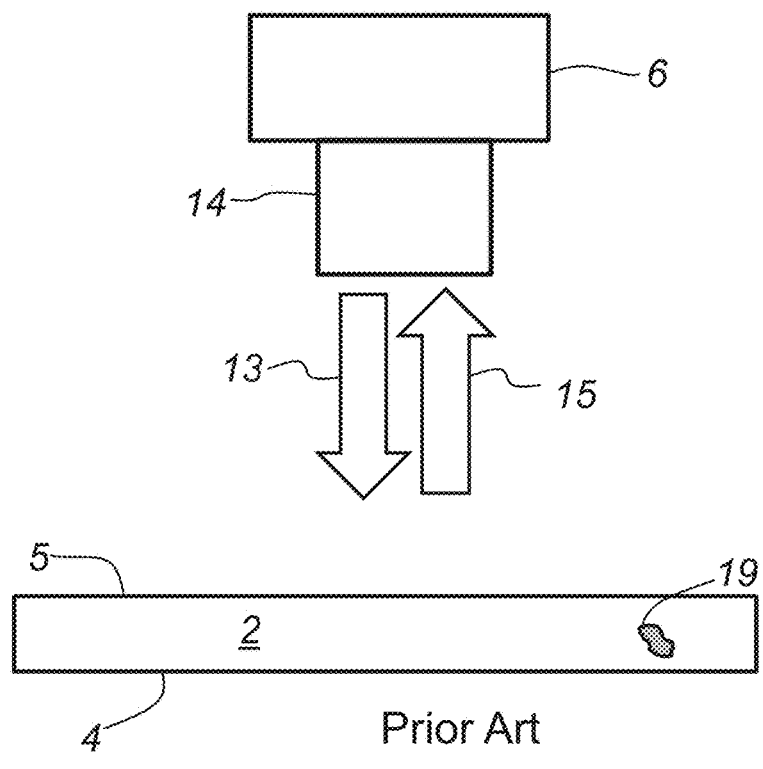
FIG. 3 is a prior art set-up for detecting interior defects by looking onto the top surface of a semiconductor device.
Figure 4:
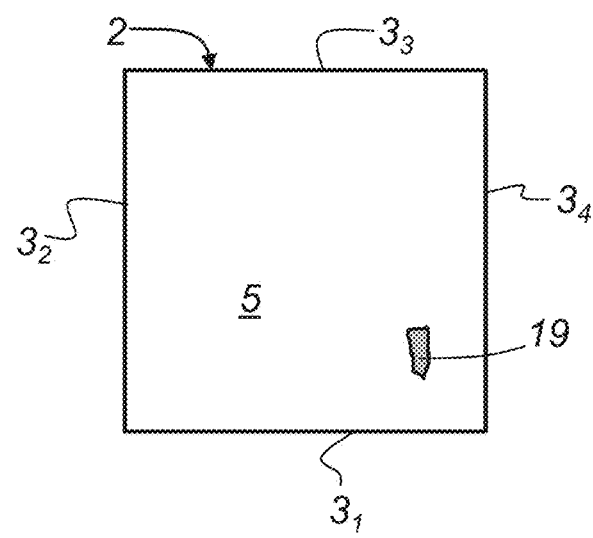
FIG. 4 is a schematic representation of an image obtained by the set-up shown in FIG. 3.

In the figures like reference numerals are used for like elements or elements of like function. Furthermore, for the sake of clarity, only those reference numerals are shown in the figures which are necessary for discussing the respective figure. The methods and apparatus described herein may be employed advantageously in conjunction with IR-light for defect inspection in semiconductor devices. Typically one would use IR light to be able to penetrate through the silicon of the semiconductor device. In other embodiments of the invention the wavelength of the light source could change. The only prerequisite is that the material of the work piece (semiconductor device) under inspection must be transparent for the wavelength range used. The description below refers to semiconductor devices, which should not be understood as a limitation of the invention. As is clear for a skilled person, the principles and ideas of the present invention are applicable to any inspection of internal or side defects of work pieces. The application of the present invention to semiconductor devices should not be regarded as a limitation.

Figure 5:
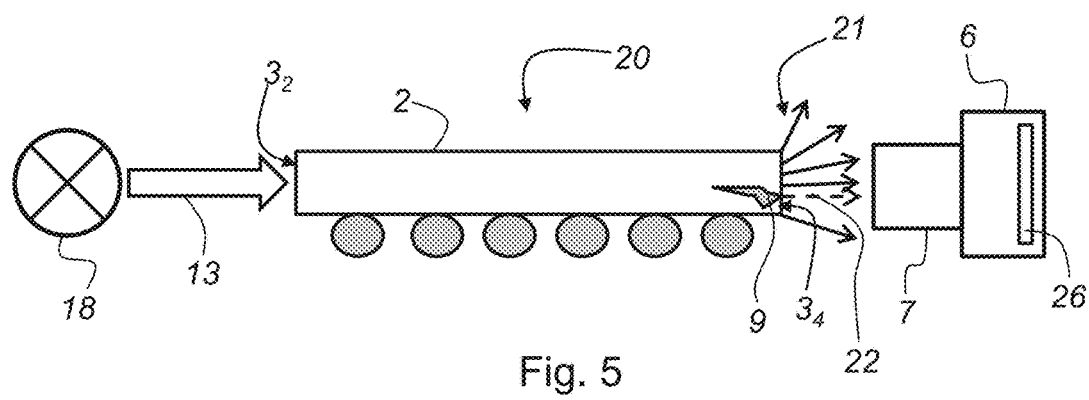
FIG. 5 is a schematic representation of an arrangement for carrying out inspection of the semiconductor device with IR illumination in side view with back-light illumination.

FIG. 5 shows a schematic representation of an arrangement 20 for carrying out inspection of the semiconductor device 2 with IR light 13. The arrangement 20 is in side view with back-light illumination. The IR light 13 generated by a light source 18 impinges perpendicularly on one selected side face $3_1$, $3_2$, $3_3$ or $3_4$ of the semiconductor device 2. It is also possible that the IR light 13 is not collimated and does not impinge perpendicularly on one selected side face $3_1$, $3_2$, $3_3$ or $3_4$ of the semiconductor device 2. With the arrangement 20 shown here it is possible to create images of the defects 9 by using IR light 13 that travels through the semiconductor device 2. The advantage of the use of IR light 13 is that one can find interior defects 9 and/or improve the signal to noise ratio for specific defects 9 of the semiconductor device 2. The camera 6 look with its lens 7 directly at one selected side face $3_3$, $3_2$, $3_3$ or $3_4$ of the semiconductor device 2. Because of the high refractive index of the silicon (n =3.5 for λ=1200nm) and the rough side face $3_1$, $3_2$, $3_3$ or $3_4$ (edge) of the semiconductor device 2 almost all the IR light 13 will enter the semiconductor device 2. While the rays of the IR light 13 will travel under small angles through the semiconductor device 2, they will exit at the opposite side face $3_1$, $3_2$, $3_3$ or $3_4$ as a diffuse ray 21 of light. In this way the semiconductor device 2 itself acts like a diffuse illuminator. However, when reaching an interior defect 9 or a side crack the normal light propagation is blocked resulting in a 'defective' part in the diffuse illumination. The blocking of the IR light 13 is represented by a dashed arrow 22. The lens 7 and the camera 6 image the side face $3_1$, $3_2$, $3_3$ or $3_4$, respectively and the interior defect 9 appears as a high contrast dark section in the camera image. The crack or the interior defect 9 is typically a disturbance in the silicon structure of the semiconductor device 2. At this disturbance the IR light 13 is reflected and does not propagate. Because of this, a detector 26 in the camera 6 will see no light coming through at the location of the interior defect 9.

Figure 6:
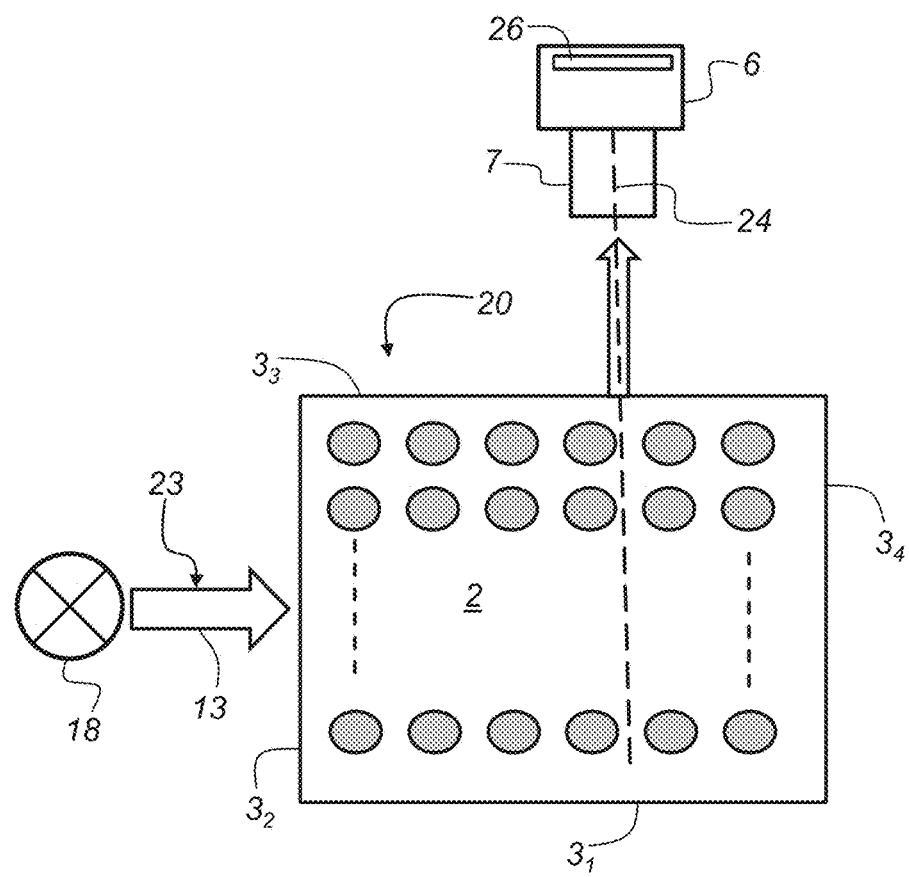
FIG. 6 is a schematic representation of an arrangement for carrying out inspection of the semiconductor device with IR illumination in side view with a dark field illumination.

Another embodiment of the arrangement 20 for carrying out inspection of the semiconductor device 2 with IR light 13 is shown in FIG. 6. Here, the inspection of the semiconductor device 2 is carried out with IR light 13 from the light source 18. The camera 6 with the lens 7 is arranged such that the camera 6 registers a dark field image of the respective side face $3_1$, $3_2$, $3_3$ or $3_4$ of the semiconductor device 2. At the second face $3_2$ a direction 23 of IR-light propagation is perpendicular to an optical axis 24 of the lens 7 of the camera 6.

Figure 7:
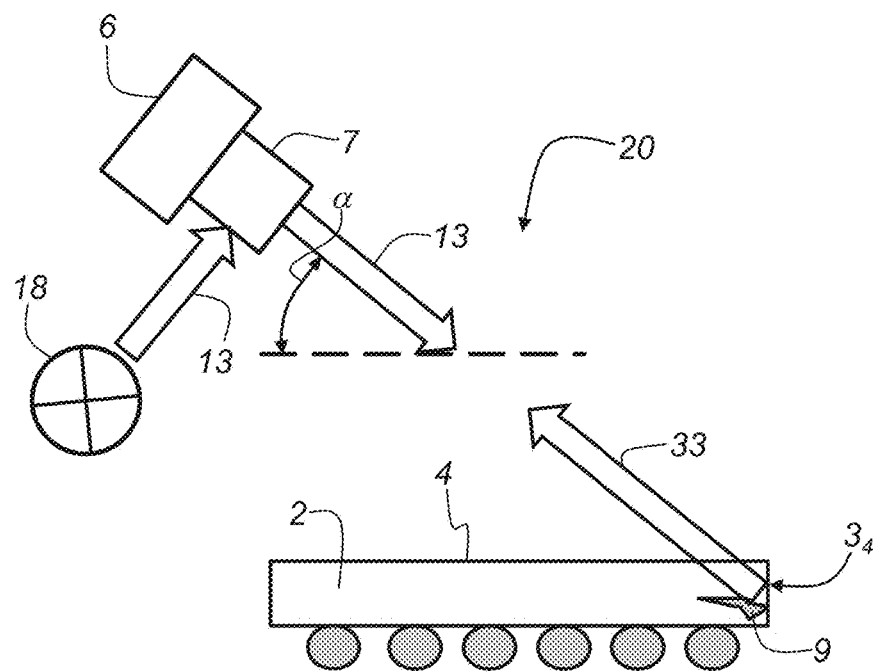
FIG. 7 is a schematic representation of an arrangement for carrying out inspection of the semiconductor device with IR illumination in angular side view with back-light illumination.

A further embodiment of the inventive arrangement 20 is shown in FIG. 7. The IR light 13 is sent from the light source 18 to the top face 4 of the semiconductor device 2 and into the semiconductor device 2 under an angle α. The IR-light 13 propagates through the semiconductor device 2 and is focused on one of the side faces $3_1$, $3_2$, $3_3$ or $3_4$ of the semiconductor device 2, respectively. The interior cracks or defects 9 block the IR-light 13 and change the normally diffuse illumination from one of the rough side faces $3_1$, $3_2$, $3_3$ or $3_4$ (see FIG. 5). The arrangement shown in FIG. 7 offers large resolution but still makes fast inspection of one of the side faces $3_1$, $3_2$, $3_3$ or $3_4$ of the semiconductor device 2 (here the fourth side face $3_4$ is inspected) possible. Every internal or side defect 9 appears bigger and higher in contrast in the image taken by camera 6 as such defects block normal internal light propagation. A diffuse IR-light 33 shining out the semiconductor device 2 has a reduced response to external contamination of semiconductor device 2 and hence increases the signal to noise ratio for the real defects 9.

As an advantageous alternative, one can move the focus of the IR-light 13 inside the semiconductor device 2, so that one can resolve interior defects 9 further away from the side faces $3_1$, $3_2$, $3_3$ or $3_4$ of the semiconductor device 2. Accordingly, one can even scan through the complete semiconductor device 2.

Figure 8:
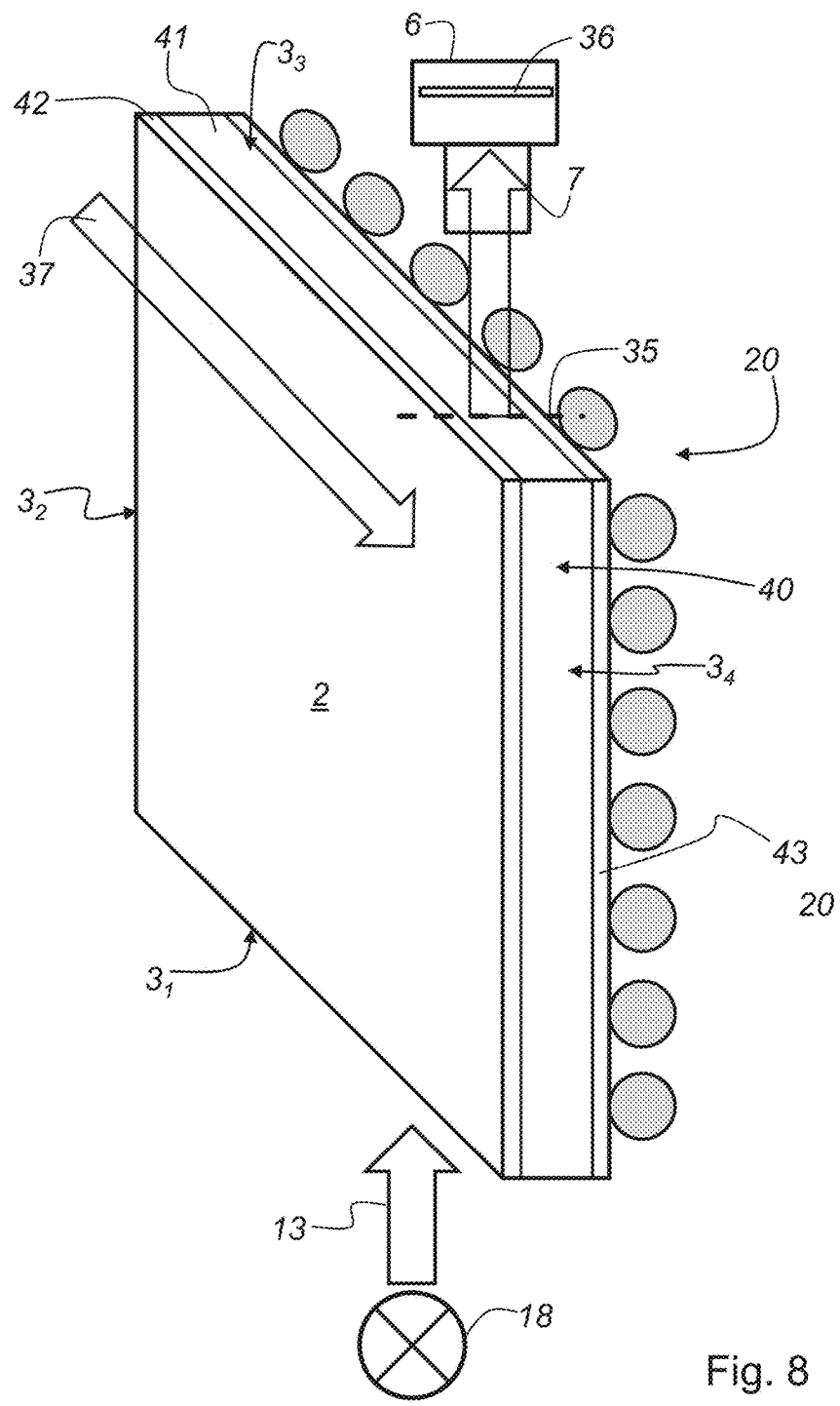
FIG. 8 is a schematic representation of an arrangement for carrying out edge inspection of a semiconductor device with IR illumination in side view and a scanning motion of the semiconductor device.

FIG. 8 shows a schematic representation of a further embodiment of an arrangement 20 of the present invention. The camera 6 has a line sensor 36 and the lens 7 images a line 35 of one of the side face $3_1$, $3_2$, $3_3$ or $3_4$ on the line sensor 36. The camera 6 is configured as a line scan camera. The camera 6 is moved along a scan direction 37. The movement can be achieved by a relative motion between the respective side face $3_1$, $3_2$, $3_3$ or $3_4$ of the semiconductor device 2 and the camera 6 along the scan direction 37, which is perpendicular to the line 35 to be imaged on the line sensor 36. The relative motion between the respective side face $3_1$, $3_2$, $3_3$ or $3_4$ of the semiconductor device 2 and the camera 6 should not be regarded as a limitation of the invention. It is clear that also only the camera or only the semiconductor device can be moved.

The semiconductor device 2 is positioned on a X, Y, Theta-stage (not shown here). The X, Y, Theta-stage is moved such that images of all four side faces $3_1$, $3_2$, $3_3$ or $3_4$ are created with the line sensor 36 of the camera 6. In the embodiment shown here, the semiconductor device 2 is composed of a bulk semiconductor layer 40 (BSL), which is optional, silicon substrate 41, a dielectric layer 42 and a metal layer 43. With the line scan camera setup high resolution images are possible which would be impossible with an area scan camera. For the side view (analog to the arrangement of FIG. 5) external IR-light 13 is shining from the light source 18 through the semiconductor device 2 (die). The IR-light 13 comes from one side face $3_1$, $3_2$, $3_3$ or $3_4$ of the semiconductor device 2 and is captured at the opposite side face $3_1$, $3_2$, $3_3$ or $3_4$ of the semiconductor device 2 by the line scan camera 6. A high resolution image is created from each side face $3_1$, $3_2$, $3_3$ or $3_4$ of the semiconductor device 2. In order to shine through the semiconductor device 2, a wavelength range is used for which the semiconductor device 2 is transparent. For a typical semiconductor device 2 (or die) this will be IR light 13.

Figure 9:
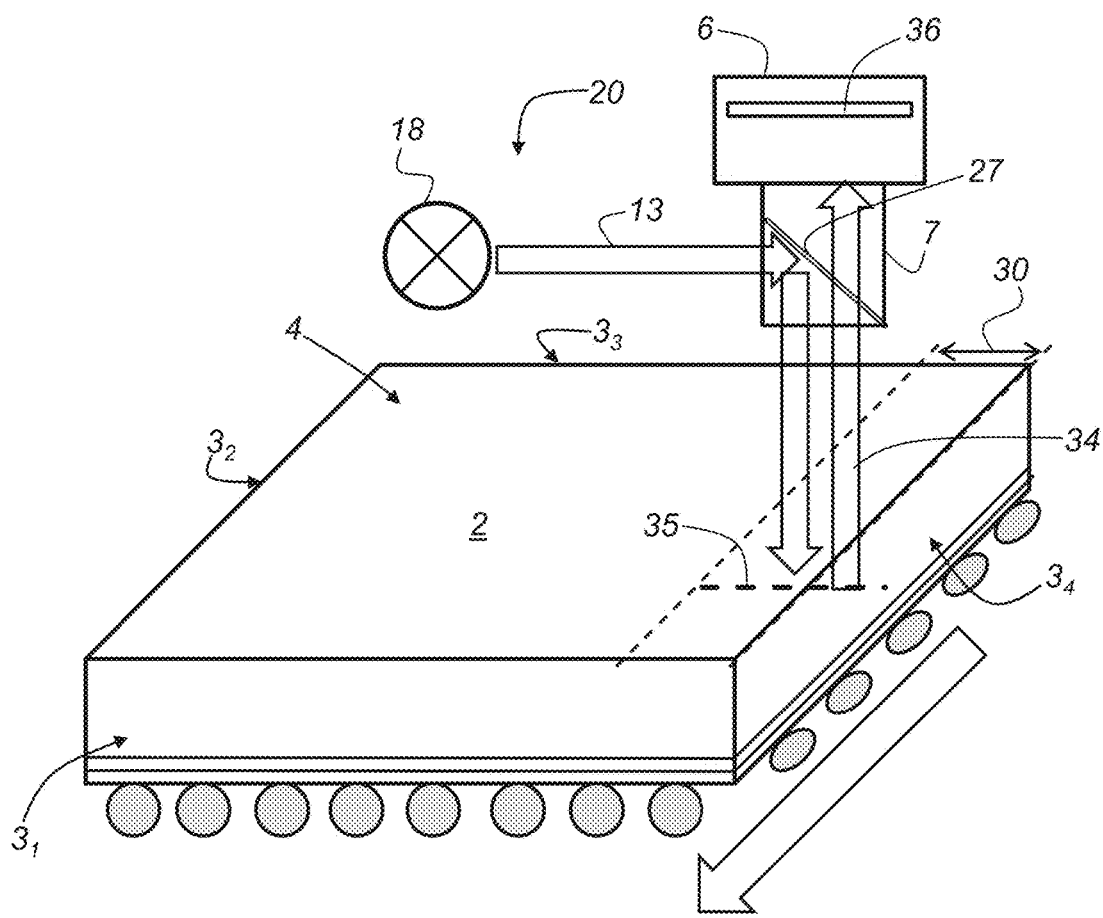
FIG. 9 is a schematic representation of an arrangement for carrying out edge inspection of a semiconductor device with IR illumination in top view and a scanning motion of the semiconductor device.

FIG. 9 shows a schematic representation of an arrangement 20 for carrying out edge inspection of a semiconductor device 2 with IR illumination in side view and a scanning motion of the semiconductor device 2. Here the camera 6 has as well a line sensor 36 and the lens 7 images a line 35 of the top face 4 close to one of the side faces $3_1$, $3_2$, $3_3$ or $3_4$ on the line sensor 36. A beam splitter 27 directs the IR-light 13 from the light source 18 onto the top face 4 of the semiconductor device 2. Coaxial returning IR light 34 from the top face 4 of the semiconductor device 2 is captured by the line sensor 36 of the camera 6. Again the movement of the semiconductor device 2 along the scan direction 37 is perpendicular to the line 35 which is imaged on the line sensor 36 of the camera 6. The movement of the semiconductor device 2 enables the creation of a top view of an edge portion 30 of the top face 4 of the semiconductor device 2 at one of the side faces $3_1$, $3_2$, $3_3$ or $3_4$. In FIG. 9 the edge portion 30 of the top face 4 is adjacent to the fourth side face 34 of the semiconductor device 2.

Figure 10:
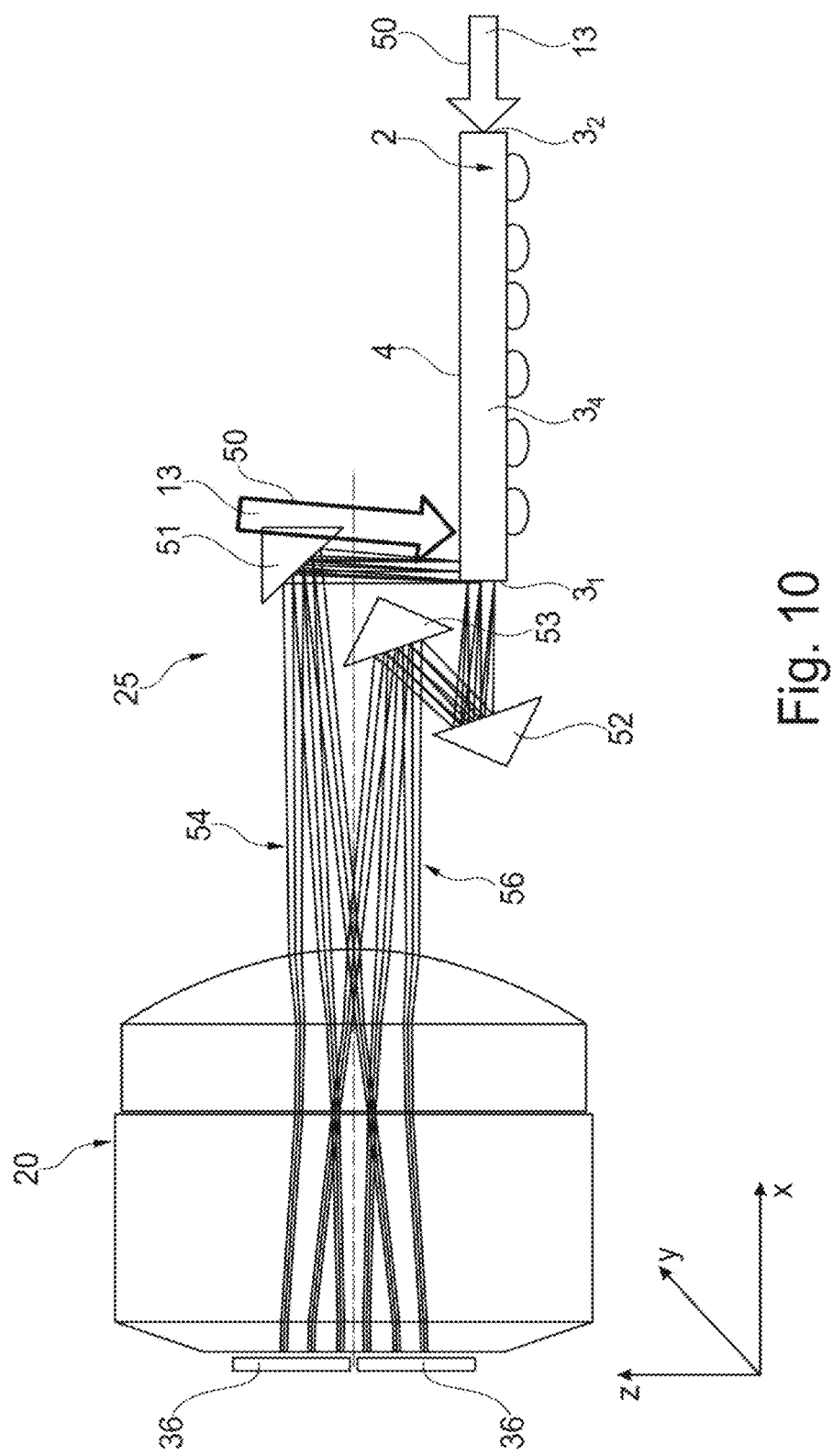
FIG. 10 is an embodiment of an arrangement for carrying out the side view and the top view of the semiconductor device, simultaneously.

The embodiment shown in FIG. 10 shows an arrangement 20 for carrying out side view and top view inspection of the semiconductor device 2, simultaneously. A special optical setup 25 is provided which allows a simultaneous view on the top face 4 and one of the side faces $3_1$, $3_2$, $3_3$ or $3_4$ of the semiconductor device 2. This optical setup 25 also allows for illumination of the top face 4 (coaxial illumination) and for illumination of one of the side faces $3_1$, $3_2$, $3_3$ or $3_4$ (external illumination) of the semiconductor device 2. The two illumination modes (coaxial and external illumination) can have the same light source or individual light sources.

By combining the view on the top face 4 and one of the side faces $3_1$, $3_2$, $3_3$ or $3_4$ of the semiconductor device 2, the images of the top face 4 and the side faces $3_1$, $3_2$, $3_3$ or $3_4$ contain much more information in order to extract the exact location and origin of the defects. By integration on a moving stage setup, high speed inspection can still be obtained although with two high resolution views.

Through the arrangement 20 and the special optical setup 25, as shown in FIG. 10, it is possible to create a simultaneous view of the edge portion 30 (see FIG. 9) of the top face 4 and one side face $3_1$, $3_2$, $3_3$ or $3_4$ of the semiconductor device 2. Additionally, two individual line sensors 36 are provided. One is used for capturing the image of a portion of the top face 4 and the other is used to capture an image of one of the side faces $3_1$, $3_2$, $3_3$ or $3_4$ which is neighboring the top face 4.

According to the embodiment shown here, light guides 50 are used for transporting the IR-light 13. The light guides 50 are positioned as close as possible to the semiconductor device 2 in order to illuminate the edge portion 30 of the top face 4 and one of neighboring the side faces $3_1$, $3_2$, $3_3$ or $3_4$ with the IR-light 13.

Figure 11:
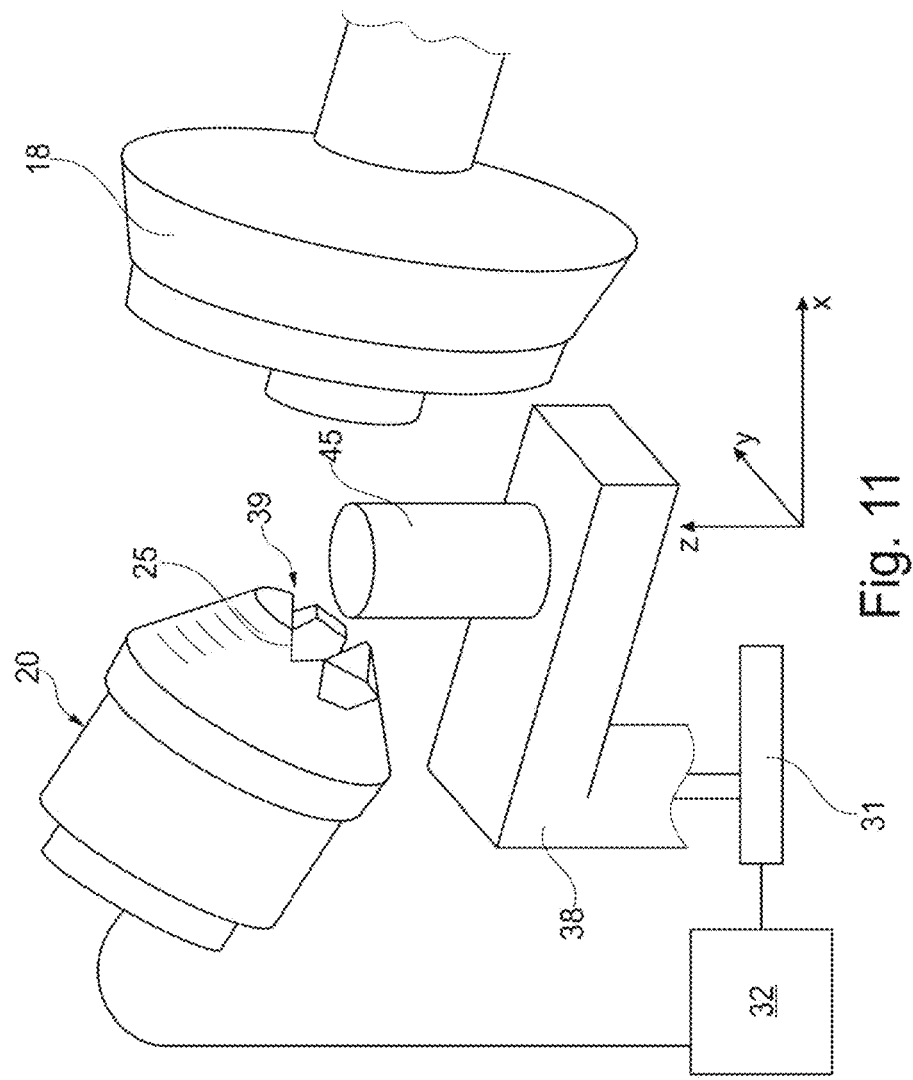
FIG. 11 is a perspective view of the arrangement for carrying out a side view of one side face of the semiconductor device.

FIG. 11 shows a perspective view of the apparatus for carrying out a side view of at least one of the side faces $3_1$, $3_2$, $3_3$ or $3_4$ of the semiconductor device 2. The semiconductor device 2 (not shown here) is placed on a hold with a chuck 45. The chuck 45 is mounted on a theta stage 38, which can be moved linearly at least in the X-coordinate direction X and the Y-coordinate direction Y. In addition a tilt is possible as well. A linear movement in the Z-coordinate direction Z can be integrated as well. A light source 18 directs the illumination light 13 to the semiconductor device 2 on the chuck 45. In the embodiment shown here, the light source 18 is arranged such that one side face $3_1$, $3_2$, $3_3$ or $3_4$ of the semiconductor device 2 is illuminated. The arrangement of the light source 18 is called backlight arrangement.

Opposite the light source 18 the arrangement 20 with the optical setup 25 is arranged in order to receive the light exiting one side face $3_1$, $3_2$, $3_3$ or $3_4$ of the semiconductor device 2 which is opposite the illuminated side face $3_1$, $3_2$, $3_3$ or $3_4$ of the semiconductor device 2. The optical setup 25 is positioned at the front end 39 of the arrangement 20. The arrangement 20 is connected to a computer 32 which receives the image data from the arrangement 20. Additionally, the computer 32 is connected to a control 31 for moving the stage 38, so that the respective side face $3_1$, $3_2$, $3_3$ or $3_4$ is scanned by the arrangement 20.

Figure 12:
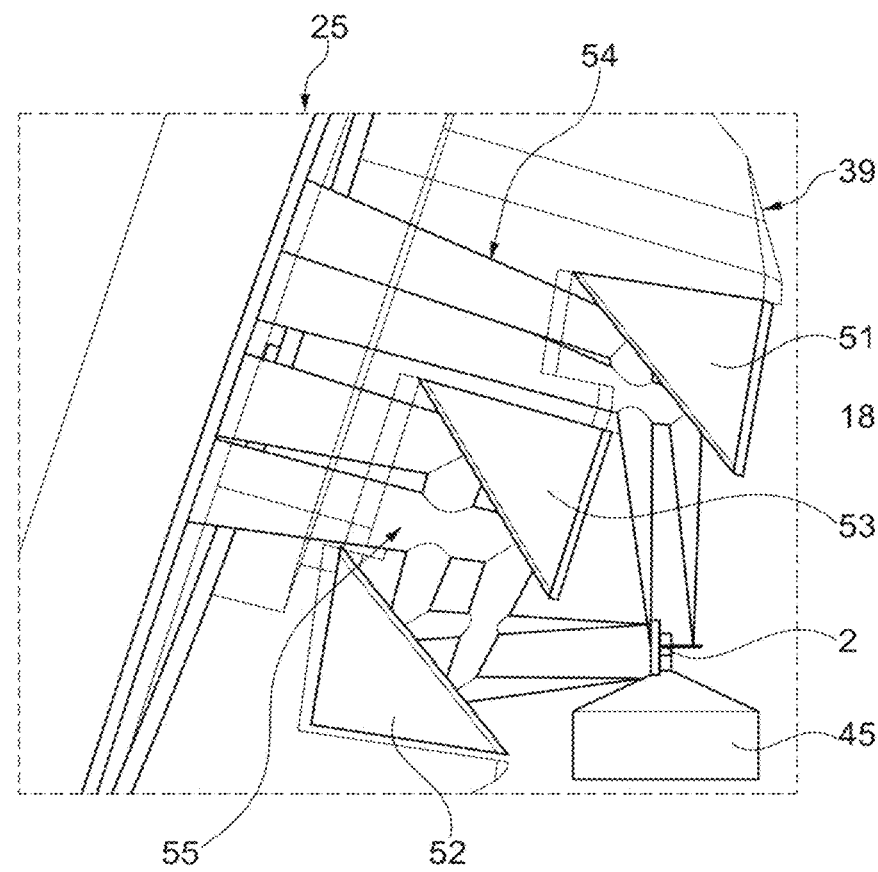
FIG. 12 is a detailed view of an opto-mechanical integration of the side view and top view inspection of the semiconductor device.

A detailed view of the optical setup 25 of the arrangement 20 is shown in FIG. 12. The optical setup 25 allows a simultaneous side view and top view inspection of the semiconductor device 2. In the embodiment shown here the optical setup 25 generates simultaneously an image of a line of light exiting a side face $3_1$, $3_2$, $3_3$ or $3_4$ of the semiconductor device 2 and an image of a line of light from at least a portion of a top face 4 of the semiconductor device 2. As already previously described the line of light from a top face 4 is positioned adjacent to the line of light of the respective side face $3_1$, $3_2$, $3_3$ or $3_4$ of the semiconductor device 2. A front end 39 of the optical setup 25 carries a top mirror 51, a first bottom mirror 52, and a second bottom mirror 53. The top mirror 51 captures an image of the line of light from a portion of the top face 4 of the semiconductor device 2. The first bottom mirror 52 and the second bottom mirror 53 are arranged such at the front end 39 of the optical setup 25 that they can capture an image of a line of light exiting from a side face of the semiconductor device 2. The optical setup 25 is designed such that the image of a line of light, exiting from a side face $3_1$, $3_2$, $3_3$ or $3_4$ of the semiconductor device 2 and the image of a line of light from a top face 4 of the semiconductor device 2 are simultaneously in focus. The optical light coupling is in such a way that an optical path 54 via the top mirror 51 and an optical path 55 via first bottom mirror 52 and second bottom mirror 53 can be lighted separately.

The process to inspect the four side faces $3_1$, $3_2$, $3_3$ or $3_4$ and/or the edge portion 30 of the top face 4 is shown in FIGS. 13A to 13E. In case one inspects the four side faces $3_1$, $3_2$, $3_3$ or $3_4$ and the edge portion 30 of the top face 4 neighboring the respective side face $3_1$, $3_2$, $3_3$ or $3_4$ one gets a combined side and top view image. The stage 38 carries out a motion profile as described in the embodiment of FIG. 13A to 13E. In FIG. 13A the semiconductor device 2 is placed on the stage 38. As described above the semiconductor device 2 can be held as well by a chuck (not shown here), which itself is mounted on the stage 38 (theta stage).

In FIG. 13B the first side face $3_1$ is parallel to an image plane 44 of the camera 6. A linear, relative movement 46 is carried out between the stage 38 with the semiconductor device 2 and the camera 6. During the movement 46 the image plane 44 of the camera 6 remains parallel to the first side face $3_1$. After the scanning of the first side face $3_1$ is finalized, the stage 38 is rotated by 90° in the clockwise direction, so that the second side face $3_2$ of the semiconductor device 2 is parallel to the image plane 44 of the camera 6 (see FIG. 13C). As shown in FIG. 13C an opposite, linear, relative movement 46 is carried out between the stage 38 with the semiconductor device 2 and the camera 6. During the movement 46 the image plane 44 of the camera 6 is parallel to the second side face $3_2$. After the scanning of the second side face $3_2$ is finalized, the stage 38 is rotated by 90° so that the third side face $3_3$ of the semiconductor device 2 is parallel to the image plane 44 of the camera 6 (see FIG. 13D). As shown in FIG. 13D a linear, relative movement 46 is carried out between the stage 38 with the semiconductor device 2 and the camera 6. During the movement 46 the image plane 44 of the camera 6 is parallel to the third side face $3_3$. After the scanning of the third side face $3_3$ is finalized, the stage 38 is rotated by 90° so that the fourth side face $3_4$ of the semiconductor device 2 is parallel to the image plane 44 of the camera 6 (see FIG. 13E). As shown in FIG. 13E, an opposite, linear, relative movement 46 is carried out between the stage 38 with the semiconductor device 2 and the camera 6. During the movement 46 the image plane 44 of the camera 6 is parallel to the fourth side face $3_4$.

As described above, the arrangement 20 and special optical setup 25 enable as well image capture of an edge portion 30 of the top face 4 of the semiconductor device 2, wherein the edge portion 30 (see FIG. 9) of the top face 4 is adjacent the respective side face $3_1$, $3_2$, $3_3$ or $3_4$ of the semiconductor device 2.

An additional embodiment of the process for scanning at least the four side faces $3_1$, $3_2$, $3_3$ or $3_4$ of the semiconductor device 2 is shown in FIGS. 14A to 14F. The movement of the stage (not shown here) and the semiconductor device 2, respectively, is composed of a rotational movement 56 around the center 58 of the semiconductor device 2 and a linear movement 57 of the semiconductor device 2 in the X/Y-plane, defined by the X-coordinate direction X and the Y-coordinate direction Y. FIG. 14A shows the starting point of the process to scan the four side faces $3_1$, $3_2$, $3_3$ or $3_4$ of the semiconductor device 2. A focus point 59 of the camera (not shown here) is on the first side face $3_1$. FIG. 14B shows the beginning of the rotational movement 56. The center 58 of the semiconductor device 2 is subjected to the movement 57 in the X/Y-plane simultaneously, so that the focus point 59 remains on the first side face $3_1$ during the rotational movement 56. FIGS. 14C to 14E show various stages of the rotational movement 56 of the semiconductor device 2, wherein the focus point 59 remains on the second side face $3_2$ during the rotational movement 56. FIG. 14F shows the situation that the focus point 59 has reached the third side face $3_3$ and is kept on the third side face $3_3$ during the rotational movement 56 of the semiconductor device 2.

The computer 32, as shown in FIG. 11, coordinates the rotational movement 56 and the simultaneous movement 57 in the X/Y-plane, so that after a rotation of 360° of the semiconductor device 2 all four side faces $3_1$, $3_2$, $3_3$ and $3_4$ have been imaged by the arrangement 20. Furthermore, the computer 32 makes sure that the focus point 59 is maintained on all four side faces $3_1$, $3_2$, $3_3$ and $3_4$ during the full 360° rotation, so that a high quality image of all four side faces $3_1$, $3_2$, $3_3$ and $3_4$ is obtained.

It is believed that the apparatus, the method and computer program of the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

LIST OF REFERENCE NUMERALS 2 work piece, semiconductor device
$3_1$ first side face
$3_2$ second side face
$3_3$ third side face
$3_4$ fourth side face
4 top face
5 bottom face
6 camera
7 lens
8 mirror
9 defect, interior defect
10 image
11 optical length
12 optical length
13 IR light, illumination light
14 optics
15 returning IR-light
16 schematic image
18 light source 19 defect
20 arrangement
21 diffuse ray
22 dashed arrow
23 direction of light propagation
24 optical axis
25 special optical setup
26 detector
27 beam splitter
30 edge portion
31 control
32 computer
33 diffuse IR-light
34 returning IR-light
35 line
36 line sensor
37 scan direction
38 stage, theta stage
39 front end
40 bulk semiconductor layer
41 silicon substrate
42 dielectric layer
43 metal layer
44 image plane
45 chuck
46 linear relative movement
50 light guide
51 top mirror
52 first bottom mirror
53 second bottom mirror
54 optical path
55 optical path
56 rotational movement (Vorsicht in FIG. 10)
57 movement
58 center
59 focus point
X X-coordinate direction
Y Y-coordinate direction
Z Z-coordinate direction
α angle

What is claimed is:

1. An apparatus for defect detection in a work piece comprising:
    at least one light source for providing illumination of a wavelength range transparent to the work piece, wherein the light source is configured to direct illumination onto the work piece at a surface of a first face of the work piece and transmit the illumination through the work piece, wherein at least a portion of the illumination transmitted through the work piece is internally reflected by at least one of a top surface or a bottom surface of the work piece before exiting the work piece at a surface of a second face of the work piece opposite the first face, wherein one or more defects block illumination from exiting the second face of the work piece;
    a camera including a lens and a detector for collecting the illumination transmitted through the work piece and exiting from the surface of the second face of the work piece, wherein the camera is configured to image one or more defects within the work piece based on the collected illumination exited through the surface of the second face of work piece and the illumination blocked by the one or more defects; and
    a stage for moving the work piece, wherein the stage and the camera are configured to impart a relative motion between the work piece and the camera to form one or more images from the illumination transmitted through the work piece and exiting from the surface of the second face of the work piece.

2. The apparatus as claimed in claim 1, wherein the second face of the work piece is oriented to the first face of the work piece such that a dark-field image is obtainable.

3. The apparatus as claimed in claim 1, wherein the at least one light source is arranged such that the illumination is directed to a top face of the work piece and the camera receives the illumination from the top face of the work piece.

4. The apparatus as claimed in claim 1, wherein the detector of the camera is a line sensor and the camera is configured as a line scan camera.

5. The apparatus as claimed in claim 4, wherein a lens of the camera is configured to image a line of illumination exiting from a side face of the work piece onto the line sensor, wherein the illumination exiting from the side face originates from at least one illumination source arranged such that back-light illumination is obtained.

6. The apparatus as claimed in claim 5, wherein a stage, that holds the work piece, is configured to move along a scan direction that is perpendicular to the line to be imaged, such that a complete image of one or more side faces of the work piece is generated.

7. The apparatus as claimed in claim 4, wherein a lens of the camera is configured to image a line of illumination from at least a portion of a top face of the work piece onto the line sensor, wherein the line of illumination is positioned adjacent to a side face of the work piece and the at least one light source is arranged such that the illumination from the top face is coaxial to the illumination directed onto the top face of the work piece.

8. The apparatus as claimed in claim 7, wherein a stage, that holds the work piece, is configured to move along a scan direction, that is perpendicular to the line, such that a complete image of a portion of the top face, adjacent to at least one side face of the work piece, is generated.

9. The apparatus as claimed in claim 4, wherein an optical setup is provided to generate simultaneously an image of a line of illumination exiting from a side face of the work piece and an image of a line of illumination from a top face of the work piece, wherein the line of illumination from the top face is positioned adjacent to the line of illumination of the respective side face of the work piece.

10. The apparatus as claimed in claim 9, wherein a front end of the optical setup carries a top mirror and a first bottom mirror and a second bottom mirror, the top mirror captures an image of the line of illumination from a portion of the top face of the work piece and the first bottom mirror and the second bottom mirror capture an image of a line of illumination exiting from a side face of the work piece.

11. The apparatus as claimed in claim 9, wherein the optical setup is designed such that the image of a line of illumination exiting from a side face of the work piece and the image of a line of illumination from a top face of the work piece are simultaneously in focus.

12. The apparatus as claimed in claim 9, wherein illumination from the at least one light source is coupled separately to a side face of the work piece and the top face of the work piece.

13. The apparatus as claimed in claim 1, wherein a light guide is positioned between the at least one light source and at least one of a top face or a side face of the work piece.

14. The apparatus as claimed in claim 1, wherein the work piece is a singulated semiconductor device.

15. The apparatus as claimed in claim 14, wherein the wavelength range of the illumination comprises infrared light.

16. An apparatus for defect detection in a work piece comprising:
- at least one light source for providing illumination of a wavelength range transparent to the work piece, wherein the at least one light source is configured to direct illumination onto the work piece at a surface of a first face of the workpiece and transmit the illumination through the work piece, wherein at least a portion of the illumination transmitted through the work piece is internally reflected by at least one of a top surface or a bottom surface of the work piece before exiting the work piece at a surface of a second face of the workpiece opposite the first face, wherein the one or more defects block illumination from exiting the second face of the workpiece;
- a camera, including a lens and a line sensor, for collecting the illumination transmitted through the work piece and exiting from the surface of the second face of the work piece, wherein the camera is configured to image one or more defects within the workpiece based on the collected illumination exited through the surface of the second face of work piece and the illumination blocked by the one or more defects;
- a chuck for holding the work piece;
- a stage for carrying the chuck; and
- a control connected to a computer for providing a relative movement between the stage with the work piece and the camera, wherein the stage and the camera are configured to impart a relative motion between the work piece and the camera to form one or more images from the illumination transmitted through the work piece and exiting from the surface of the second face of the work piece.

17. The apparatus as claimed in claim 16, wherein the stage is configured to move such that a focus of the camera is on a respective side face during the entire movement of the stage.

18. The apparatus as claimed in claim 16, wherein the second face of the work piece is oriented to the first face of the work piece such that a dark field image of the second face is obtainable.

19. The apparatus as claimed in claim 16, wherein a light guide is used to guide the illumination from the at least one light source to a respective side face of the work piece.

20. The apparatus as claimed in claim 16, wherein the work piece comprises a singulated semiconductor device.

21. The apparatus as claimed in claim 20, wherein the wavelength range of the illumination comprises infrared light.

22. An apparatus for defect detection in a work piece comprising:
- at least one light source for providing illumination of a wavelength range transparent to the work piece, wherein the light source is configured to direct illumination onto the work piece at a surface of a first edge of the workpiece and transmit the illumination through the work piece, wherein at least a portion of the illumination transmitted through the work piece is internally reflected by at least one of a top surface or a bottom surface of the work piece before exiting the work piece at a surface of a second edge of the workpiece opposite the first edge, wherein one or more defects block illumination from exiting the second edge of the workpiece; and
- a camera including a lens and a detector for collecting the illumination transmitted through the work piece and exiting from the surface of the second edge of the work piece, wherein the camera is further configured to image one or more defects within the workpiece based on the collected illumination exited through the surface of the second edge of work piece and the illumination blocked by the one or more defects.

* * * * *